US00PP28142P3

(12) United States Plant Patent
Brown

(10) Patent No.: US PP28,142 P3
(45) Date of Patent: Jun. 27, 2017

(54) ***ABUTILON* PLANT NAMED 'PASSION'**

(50) Latin Name: *Abutilon×hybrida*
Varietal Denomination: Passion

(71) Applicant: NuFlora International Pty. Ltd., Macquarie Fields (AU)

(72) Inventor: Graham Brown, Pennant Hills (AU)

(73) Assignee: NuFlora International Pty Ltd, Macquarie Fields, NSW (AU)

( * ) Notice: Subject to any disclaimer, the term of this patent is extended or adjusted under 35 U.S.C. 154(b) by 0 days.

(21) Appl. No.: 14/999,352

(22) Filed: Apr. 27, 2016

(65) Prior Publication Data

US 2016/0338237 P1 Nov. 17, 2016

(30) Foreign Application Priority Data

May 15, 2015 (AU) ..... PBR 2015/106

(51) Int. Cl.
*A01H 5/02* (2006.01)

(52) U.S. Cl.
USPC ..... Plt./263.1

(58) Field of Classification Search
USPC ..... Plt./263.1
See application file for complete search history.

*Primary Examiner* — Annette Para
(74) *Attorney, Agent, or Firm* — Barbara Campbell; James M. Weatherly; Cochran Freund & Young, LLC

(57) ABSTRACT

A new cultivar of *Abutilon* named 'Passion' that is characterized by a compact freely-branching habit and watermelon-pink flowers produced continually from spring until fall, and bearing prominent yellow staminal tube and anthers and cream to pale-green calyces.

2 Drawing Sheets

Genus and species: *Abutilon×hybrida.*
Variety denomination: 'Passion'.

CROSS-REFERENCE TO RELATED APPLICATIONS

This application claims the benefit of priority to a Plant Breeders Rights application filed with the Australian government, application number 2015/106, filed on May 15, 2015.

BACKGROUND OF THE NEW PLANT

The present invention relates to a new and distinct cultivar of *Abutilon×hybrida*, commonly known as Chinese lantern. The new cultivar is in the family Malvaceae. Known botanically as *Abutilon×hybrida*, the new variety will be referred to hereinafter by the cultivar name 'Passion'.

'Passion' is the result of a breeding program that commenced in 2000 in Cobbitty, New South Wales, Australia. The objectives of the breeding program were to develop compact forms of *Abutilon* with significantly improved flowering characteristics, particularly a long flowering period, floriferous nature, and a wide range of flower color presented well at the time of sale.

'Passion' is a seedling selection resulting from the controlled cross-pollination of two parents which had been raised and retained by the inventor for breeding purposes. The female parent is an individual seedling known to the inventor as 'x05.1.1' (unreleased and unpatented). The male parent is an individual seedling known to the inventor as 'x05.1.2' (unreleased and unpatented). Cross-pollination was conducted by the inventor during January 2008. The resulting seed was collected, sown and grown out by the inventor. In October 2008, the inventor selected 'Passion' for its combination of well-presented flowers borne on plants with a natural self-branching habit. In addition, the inventor selected 'Passion' for its bright flower color and its early and sustained profuse flowering.

'Passion' was first asexually propagated by the inventor in October 2008 in Cobbitty, New South Wales, Australia. Asexual propagation was accomplished using softwood cuttings. Since that time, under careful observation, the distinguishing characteristics of 'Passion' have been determined stable and uniform, and to reproduce true to type in successive generations of asexual propagation.

SUMMARY

The following represent the distinguishing characteristics of the new *Abutilon* cultivar named 'Passion'. 'Passion' has not been tested under all possible conditions and phenotypic differences may be observed with variations in environmental, climatic, and cultural conditions, however, without any variance in genotype.

1. The growth habit of 'Passion' is compact due to its short internodes and freely branching structure.
2. 'Passion' achieves a height of 30 cm and a spread of 35 cm in the first year of growth in a 1 gallon container.
3. 'Passion' achieves a height of 55 cm and a spread of 60 cm at maturity in a 3-gallon or larger containers.
4. The stems of 'Passion' are strong and rigid.
5. The flowers of 'Passion' are bell-shaped, facing downward and outward.
6. 'Passion' produces flowers at least from spring until fall. In California, 'Passion' has been observed in flower all year around.
7. The flowers of 'Passion' are watermelon pink in color.

8. The flowers of 'Passion' bear a prominent yellow staminal tube terminating in a globular array of yellow anthers.
9. The calyces of 'Passion' are prominent cream to pale-green in color.
10. 'Passion' is perennial in temperatures above 15° Fahrenheit.

DESCRIPTION OF THE PHOTOGRAPHS

The accompanying color photographs show the overall appearance of the plant and flower of the new *Abutilon* cultivar named 'Passion'. Both photographs were made from a digital photograph of a 1-gallon plant of 'Passion' which was 23-weeks old from a cutting and which has been grown outdoors in Oxnard, Calif. The plant was not pinched or pruned and no chemical growth regulators were applied. The photographs were made using conventional techniques and although foliage and flower colors may appear different from actual colors due to light reflectance, they are as accurate as possible by photography of this type.

DESCRIPTION OF THE NEW VARIETY

Figure 1:
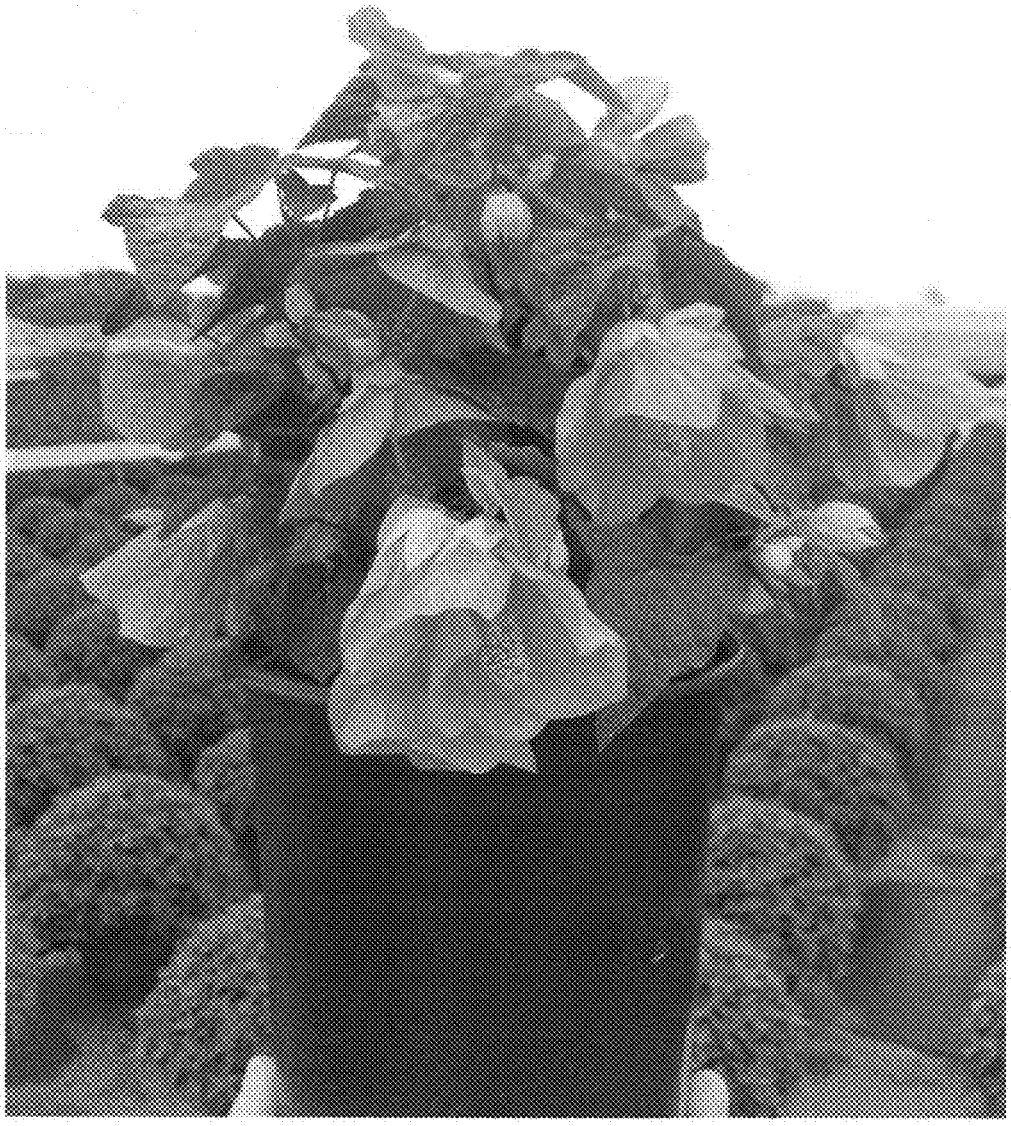
FIG. 1 depicts the compact habit of 'Passion' and the numerous watermelon-pink flowers. The non-flowering plants in rows in the background of the drawing are unrelated to 'Passion'.
Figure 2:
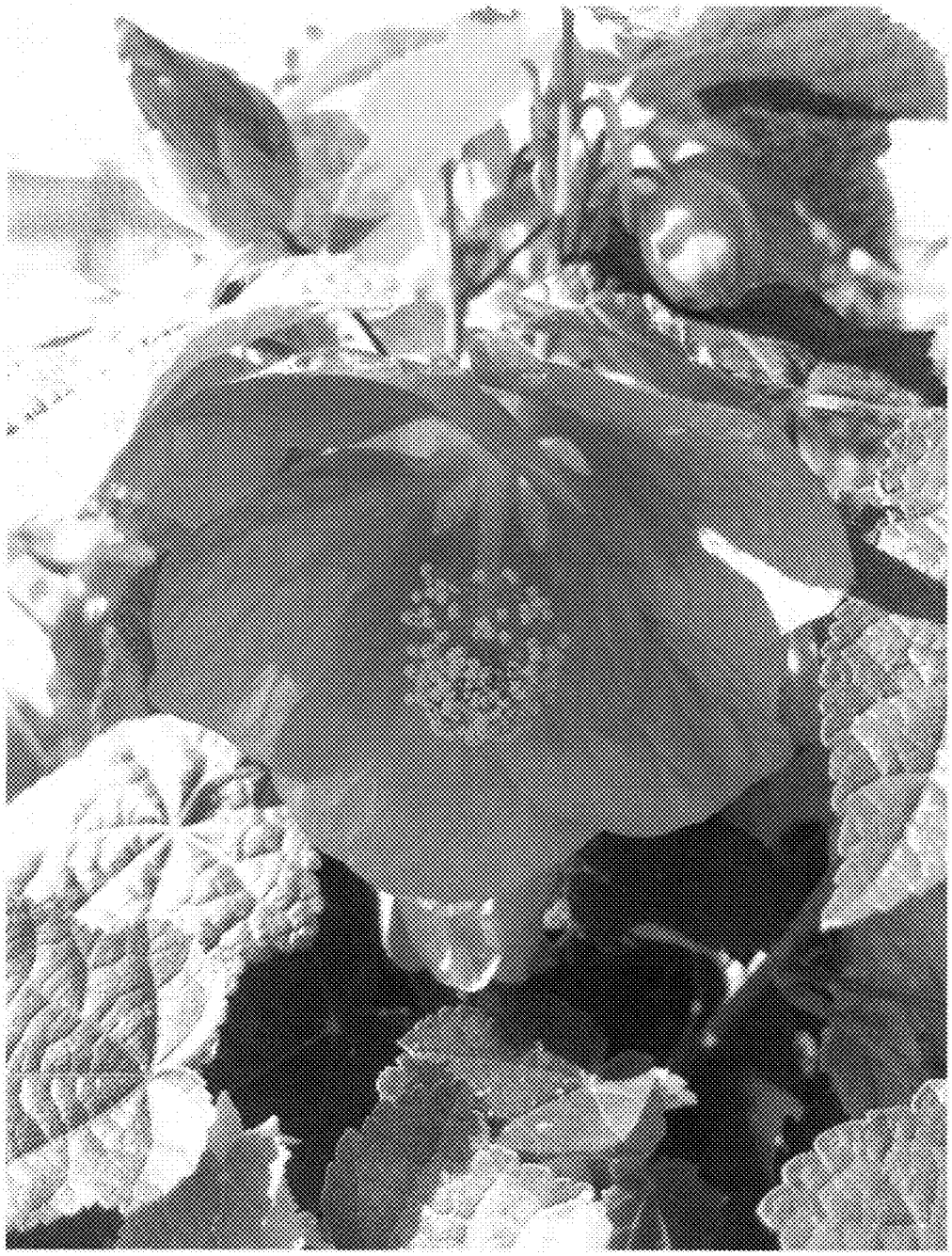
FIG. 2 depicts the buds and bud calyx of 'Passion' and the interior of a mature flower of 'Passion' with its prominent yellow staminal column and anthers.

The following is a detailed description of the *Abutilon* cultivar named 'Passion'. Data was collected in Oxnard, Calif. in August 2015 from one-year old plants grown outdoors in 1-gallon containers. Color determinations are in accordance with The Royal Horticultural Society Colour Chart 2007 except where general color terms of ordinary dictionary significance are used. The growing requirements are similar to the species.

Botanical classification:

*Genus and species.*—*Abutilon×hybrida.*
*Family.*—Malvaceae.
*Denomination.*—'Passion'.
*Common name.*—Chinese lantern.

Parentage:

*Female parent.*—Proprietary *Abutilon* seedling code 'x05.1.1' (unreleased and unpatented).
*Male parent.*—Proprietary *Abutilon* seedling code 'x05.1.2' (unreleased and unpatented).

Plant:

*Use.*—Planted containers, hanging baskets, garden border, and in the landscape.
*Vigor.*—Moderately vigorous.
*Growth habit.*—Compact, freely branching.
*Dimensions first year.*—30 cm in height and 35 cm in width.
*Dimensions at maturity.*—55 cm in height and 60 cm in width.
*Hardiness.*—USDA Zone 8.
*Propagation.*—Softwood cuttings.
*Root system.*—Fine and fibrous.
*Cultural requirements.*—Plant in full sun and well-drained soils with moderate water, drought tolerant once established.
*Type.*—Perennial.
*Time to initiate roots* (*range*).—14 to 28 days to produce roots on an initial cutting.
*Crop time* (*range*).—6 to 8 weeks to produce a 4-inch container plant from a 72 cell transplant (spring planting) and 10-12 weeks to produce a 1-liter container plant from a 72-cell transplant (spring planting).
*Seasonal interest.*—Showy flowers and calyces spring through fall.
*Pests and diseases.*—Other than hibiscus beetle and whitefly which are attracted to the genus, 'Passion' does not exhibit any notable susceptibility or resistance to pests and diseases.
*Special considerations.*—Trim back when young and after blooming to encourage strong basal branching and re-blooming.

Stem:

*Branching habit.*—Freely branching.
*Stem length* (*range*).—20 cm to 25 cm.
*Stem diameter.*—0.40 cm at base.
*Stem strength.*—Strong and rigid.
*Stem color.*—138B except stem base where woody (lignified) 146C.
*Internode length* (*average*).—1.5 cm to 2.0 cm.
*Shape.*—Cylindrical.
*Surface texture.*—Lightly pubescent, hairs fine, color 156D, length is less than 0.25 mm.

Foliage:

*Leaf arrangement.*—Alternate.
*Leaf division.*—Simple.
*Leaf margin.*—Crenate.
*Leaf shape* (*range*).—Cordate to ovate.
*Leaf base.*—Cordate.
*Leaf apex.*—Acute.
*Leaf venation.*—Pinnate.
*Vein color* (*adaxial surface*).—151A.
*Vein color* (*abaxial surface*).—144C.
*Leaf surface* (*adaxial*).—Smooth, glabrous.
*Leaf surface* (*abaxial*).—Pubescent.
*Leaf attachment.*—Petiolate.
*Petiole dimensions* (*average*).—2.50 cm in length and 1 mm in width.
*Petiole color.*—144A, except where adaxial surface is exposed to direct sunlight where color ranges between 177A and 187A.
*Petiole surface.*—Puberulent.
*Leaf length* (*mature, range*).—5.5 cm to 7.0 cm.
*Leaf width* (*range*).—4.5 cm to 5.0 cm.
*Leaf color* (*adaxial surface*).—143A.
*Leaf color* (*abaxial surface*).—138B.
*Foliar fragrance.*—Absent.

Inflorescence:

*Type.*—Simple cyme consisting of terminal flower and 2-5 flowers branching from terminal peduncle.
*Dimensions of inflorescence* (*average*).—6 Cm in length and 6 cm in width.
*Quantity of flowers per inflorescence* (*range*).—3-6 per cyme.
*Blooming season.*—Spring through fall.
*Flower arrangement.*—Clustered.
*Flower shape.*—Campanulate.
*Flower diameter* (*as growing*).—5.0 cm.
*Flower diameter* (*flower flattened*).—8 cm-9 cm.
*Flower depth* (*average*).—4.0 cm.
*Aspect.*—Pendulous.

*Persistent or self-cleaning*.—Self-cleaning.
*Flower fragrance*.—Absent.
*Bud color* (*petals first protruding*.—N34A
*Bud shape*.—Ovoid.
*Bud length*.—2.5 cm.
*Bud diameter*.—1.5 cm.
*Bud apex*.—Acute.
*Bud surface*.—Pubescent.
*Petals*.—Five in number.
*Petal shape*.—Obdeltoid.
*Petal apex*.—Obtuse.
*Petal base*.—Attenuate.
*Petal length*.—4.0 cm.
*Petal width*.—3.0 cm.
*Petal margin*.—Entire.
*Petal color* (*both surfaces*).—42A on first opening becoming 41A.
*Petals unfused or fused*.—Unfused and individually adnate to stamen column.
*Petal surface* (*abaxial and adaxial surface*).—Glabrous.
*Epicalyx*.—Absent.
*Calyx shape*.—Campanulate, 5-lobed.
*Calyx and lobe color* (*both surfaces*).—10C (bud and flower), except 149B at base of calyx of open flower.
*Calyx texture*.—Chartaceous, translucent.
*Calyx dimensions*.—1.7 cm in diameter and 2.0 cm in depth.
*Lobes*.—5 in number.
*Lobe dimensions*.—1.3 cm in length and 0.9 cm in width.
*Lobe apex*.—Broad acute.
*Lobe base*.—Truncate.
*Lobes fused or unfused*.—Basally fused.
*Lobe margin*.—Entire.
*Peduncle arrangement*.—Axillary.
*Peduncle shape*.—Cylindrical.
*Peduncle length*.—1.5 cm to 4.0 cm.
*Peduncle diameter*.—1 mm.
*Peduncle color*.—144A, except where adaxial surface is exposed to direct sunlight when color ranges between 177A and 187A.
*Peduncle surface*.—Puberulent.

Reproductive organs:

*Stamens*.—Many, fused (unable to determine quantity) to form a single pronounced staminal column inside which 12 to 15 free filaments have been observed clustered around and enclosing the styles.
*Staminal column color*.—18A.
*Staminal column dimensions*.—2.5 cm in length and 2 mm in diameter, swollen at base, diameter 3.5 mm.
*Stamen column surface*.—Smooth, glabrous.
*Filaments*.—12 to 15 free filaments observed, length 4 mm, diameter less than 0.25 mm, color 41A. Remaining filaments fused and within staminal column.
*Anthers*.—Numerous, in the range 100 to 120, globular arrangement and emerging from upper 1 cm of staminal tube.
*Anther color*.—24B.
*Shape of anther*.—Crescent-shaped.
*Dimensions of anther*.—1.5 mm in length and 1.0 mm in diameter.
*Diameter of anther globular arrangement*.—1 cm.
*Pollen quantity*.—Moderate to heavy.
*Pollen color*.—17C.
*Style*.—Approximately 5 in number, 3 cm in length, 1 mm in diameter, color N30B.
*Stigma*.—Orbicular, 0.25 mm in diameter, color 16A.
*Ovary position*.—Superior.
*Ovary shape*.—Conical.
*Ovary color*.—145B.
*Ovary dimensions*.—3 mm in height and 2.5 mm in diameter.

Seed: Only immature seed has been observed. Flowers detach prior to seed ripening. Seed quantity is approximately 20 in total, in 5 capsules each containing 3 to 5 seeds. Seed description (immature): Ovoid, length 2 mm, diameter 1.5 mm, color 157D.

COMPARISON TO PARENTAL LINES AND COMMERCIAL VARIETY

'Passion' is distinguishable from the parent selections by plant size and habit, and by flower color. In comparison with both parents, 'Passion' is shorter in height and more freely branching in habit. In addition, whereas the flowers of 'Passion' are watermelon-pink in color, the flowers of both parents are light-pink in color.

The closest comparison plant in commerce known to the inventor is the inventor's variety of *Abutilon* named 'Nuabred' (U.S. Plant Pat. No. 25,443). Whereas the flowers of 'Nuabred' are scarlet-red in color, the flowers of 'Passion' are watermelon-pink in color. In addition, in comparison with 'Nuabred', 'Passion' is more compact, more freely branching, and bears more flowers in each inflorescence and overall.

I claim:

1. A new and distinct cultivar of *Abutilon* plant named 'Passion' as described and illustrated herein.

* * * * *